United States Patent [19]

Meek et al.

[11] Plant 4,883

[45] Aug. 31, 1982

[54] CHRYSANTHEMUM PLANT

[75] Inventors: Jack M. Meek; William E. Duffett, both of Salinas, Calif.

[73] Assignee: Yoder Brothers, Inc., Barberton, Ohio

[21] Appl. No.: 164,351

[22] Filed: Jun. 30, 1980

[51] Int. Cl.[3] ..... A01H 5/00
[52] U.S. Cl. ..... Plt./74
[58] Field of Search ..... Plt./74

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum cultivar particularly characterized as to uniqueness by the combined characteristics of flat capitulum form; daisy capitulum type; dark red bronze ray floret color; yellow-green (immature) to yellow (mature) disc floret color; diameter across face of capitulum ranging from 75 to 100 mm. at maturity; uniform nine week photoperiodic flowering response to short days; tall plant height when grown as a single stem cut spray; medium peduncle length, and semi-upright branching pattern.

1 Drawing Figure

1

The present invention comprises a new and distinct cultivar of *Chrysanthemum morifolium,* Ramat., hereinafter referred to by the cultivar name Accord.

Accord is an induced mutation of Accent, disclosed in U.S. Plant Pat. No. 3,945, and was selected to expand the color range of the parental variety.

Accord was discovered and selected as one flowering plant within a flowering block of the parental seedling by Jack M. Meek on July 12, 1977 in a controlled environment in Barberton, Ohio. Plants within the flowering block were derived from stock plants which had been irradiated as unrooted cuttings with an X-ray source of 2600 R units.

The first act of asexual reproduction of Accord was accomplished when vegetative cuttings were taken from the initial selection in January, 1978 in a controlled environment in Salinas, Calif. by a technician working under formulations established and supervised by Jack M. Meek and William E. Duffett. Continued asexual reproduction by vegetative cuttings for evaluative tests in flowering and stock programs in conjunction with horticultural examination of selected plants initiated on Aug. 15, 1978 has demonstrated that the combination of characteristics as herein disclosed for Accord are firmly fixed and are retained through successive generations of asexual reproduction.

Accord has not been observed under all possible environmental conditions. The phenotype may vary significantly with variations in environment such as temperature, light intensity and day length. The following observations, measurements and comparisons describe plants grown in Salinas, Calif. under greenhouse conditions which approximate those generally used in commercial practice.

The following traits have been repeatedly observed and are determined to be basic characteristics of Accord which in combination distinguish this chrysanthemum as a new and distinct cultivar:

(1) flat capitulum form;

(2) daisy capitulum type;

(3) dark red bronze ray floret color;

(4) yellow-green (immature) to yellow (mature) disc floret color;

(5) diameter across face of capitulum ranging from 75 to 100 mm. at maturity;

2

(6) uniform nine week photoperiodic flowering response to short days;

(7) tall plant height (attaining a height as a flowered plant of 90 to 95 cm. from a rooted cutting planted to short days for April through November flowerings);

(8) short peduncle length; and (9) semi-upright branching pattern.

Of the many commercial cultivars known to the present inventors, the most similar in comparison to Accord is the parental cultivar Accent. Reference is made to attached Chart A which compares certain characteristics of Accord to those same characteristics of Accent. Compared generally to Accent, Accord has different ray floret color and taller plant height. The capitulum form, capitulum type, diameter across face of capitulum, flowering response period and peduncle length of Accord are similar to those same characteristics of Accent.

The accompanying photographic drawing shows typical inflorescence characteristics of Accord, with the colors being as nearly true as possible with illustrations of this type.

In the following description, color references are made to The Royal Horticultural Society Colour Chart. The color values were determined between 8:00 and 8:30 a.m. on June 5, 1980 under 100 foot-candle light intensity at Salinas, Calif.

Classification:

*Botanical.*—*Chrysanthemum morifolium,* Ramat., cv Accord.

*Commercial.*—Cut daisy spray.

I. INFLORESCENCE

A. Capitulum:

*Form.*—Flat.

*Type.*—Daisy.

*Diameter across face.*—75 to 100 mm.

B. Corolla of ray florets:

*Color, general tonality from a distance of three meters.*—45-A to 45-C.

*Color (abaxial).*—45-A to 42-A over 179-A.

*Color (adaxial).*—42-A over 179-A.

C. Corolla of disc florets:

*Color (immature).*—144-A.

*Color (mature).*—15-B.

D. Reproductive organs:

*Androecium.*—Present disc florets only; scant pollen.

*Gynoecium.*—Present both ray and disc florets.

II. PLANT

A. General appearance:

*Height.*—Tall, 15 to 20 cm., taller than Accent (medium height).

*Branching pattern.*—Semi-upright.

B. Foliage:

*Color (abaxial).*—Approximately 137-A to 137-B but more greyed.

*Color (adaxial).*—138-A but duller and more greyed.

*Shape.*—Spatulate; deeply lobed.

CHART A

COMPARISON OF ACCORD AND ACCENT

| CULTIVAR | RAY FLORET COLOR | CAPITULUM FORM & TYPE | DIAMETER ACROSS FACE OF CAPITULUM |
|---|---|---|---|
| Accord | Dark Red Bronze | Flat Daisy | 75 to 100 mm. |
| Accent | Purple | Flat Daisy | 75 to 100 mm. |

CHART A-continued

COMPARISON OF ACCORD AND ACCENT

| CULTIVAR | PLANT HEIGHT | FLOWERING RESPONSE PERIOD | PEDUNCLE LENGTH |
|---|---|---|---|
| Accord | Tall 90 to 95 cm. | 9 week | Short 5 to 8 cm. |
| Accent | Medium 75 to 80 cm. | 9 week | Short 5 to 8 cm. |

COMPARISONS MADE OF PLANTS GROWN AS SINGLE STEM CUT SPRAYS WITH NO LONG DAYS IN SALINAS, CALIFORNIA

We claim:

1. A new and distinct cultivar *Chrysanthemum morifolium,* Ramat., plant known by the cultivar name Accord, as described and illustrated, and particularly characterized as to uniqueness by the combined characteristics of flat capitulum form; daisy capitulum type; dark red bronze ray floret color; yellow-green (immature) to yellow (mature) disc floret color; diameter across face of capitulum ranging from 75 to 100 mm. at maturity; uniform nine week photoperiodic flowering response to short days; tall plant height, short peduncle length; and semi-upright branching pattern.

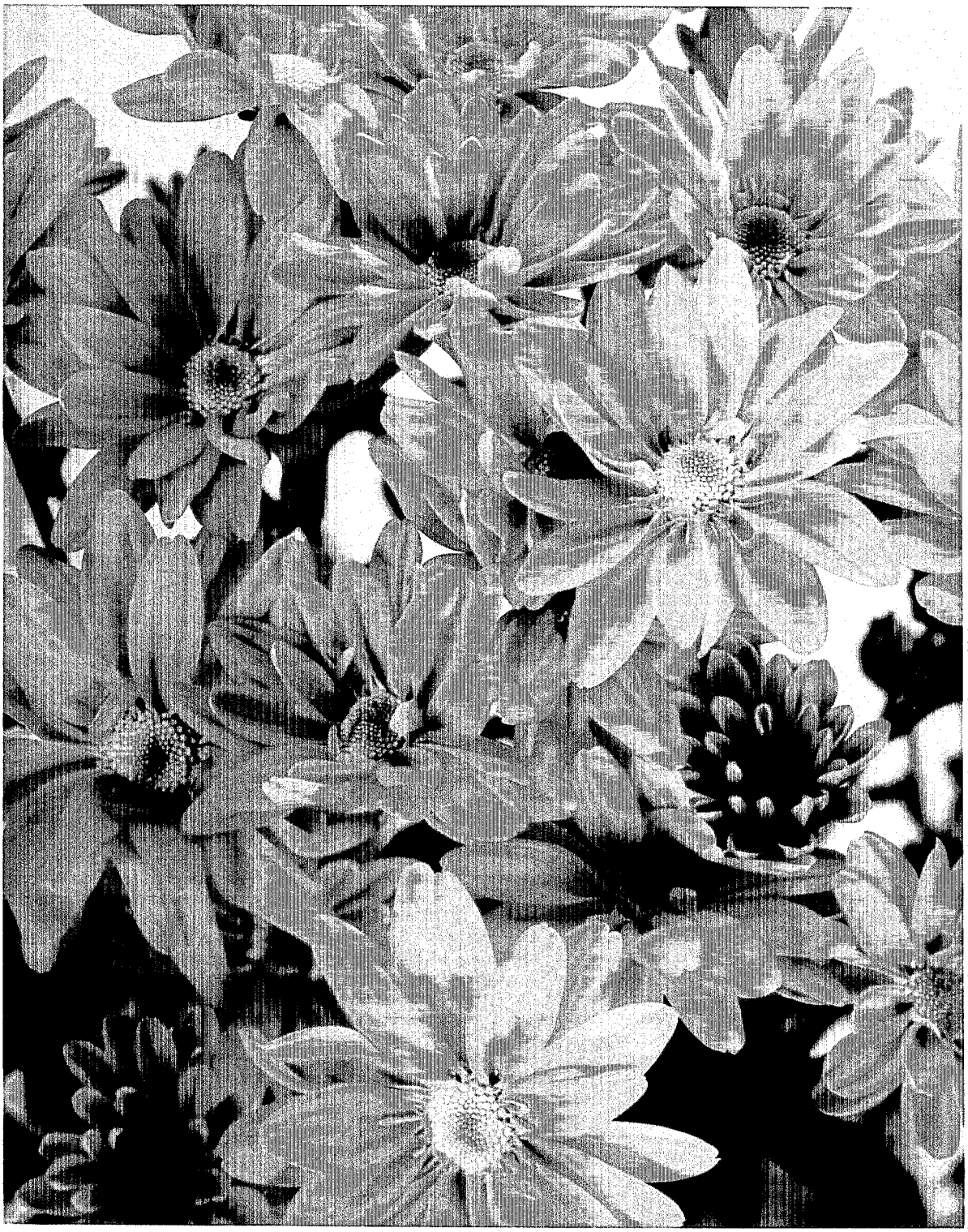

* * * * *